United States Patent
Sun et al.

(10) Patent No.: US 11,408,875 B2
(45) Date of Patent: Aug. 9, 2022

(54) METHOD FOR DETECTING AND IDENTIFYING TOXIC AND HARMFUL GASES BASED ON MACHINE OLFACTION

(71) Applicant: GUANGDONG UNIVERSITY OF TECHNOLOGY, Guangdong (CN)

(72) Inventors: Yunlong Sun, Guangdong (CN); Dehan Luo, Guangdong (CN); Hui Li, Guangdong (CN)

(73) Assignee: GUANGZHOU DEXIN SEMICONDUCTOR TECHNOLOGY CO. LTD, Guangzhou (CN)

( * ) Notice: Subject to any disclaimer, the term of this patent is extended or adjusted under 35 U.S.C. 154(b) by 297 days.

(21) Appl. No.: 16/804,477

(22) Filed: Feb. 28, 2020

(65) Prior Publication Data

US 2020/0200724 A1    Jun. 25, 2020

Related U.S. Application Data

(63) Continuation of application No. PCT/CN2017/107087, filed on Oct. 20, 2017.

(30) Foreign Application Priority Data

Aug. 30, 2017 (CN) .......................... 201710785985.7

(51) Int. Cl.
*G01N 33/00* (2006.01)

(52) U.S. Cl.
CPC . *G01N 33/0062* (2013.01); *G01N 2033/0068* (2013.01)

(58) Field of Classification Search
CPC .......... G01N 33/0031; G01N 33/0034; G01N 33/0032; G01N 33/0075;
(Continued)

(56) References Cited

U.S. PATENT DOCUMENTS 7,693,049 B2    4/2010    Joseph et al.
9,643,186 B1 *  5/2017    Ahmad ..................... B01L 3/52
(Continued)

FOREIGN PATENT DOCUMENTS

CN    102279213 A  * 12/2011
CN    103499608 A    1/2014
(Continued)

*Primary Examiner* — Jeffrey P Aiello

(57) ABSTRACT

Disclosed is a method for detecting and identifying toxic and harmful gases based on machine olfactory. Information about the toxic and harmful gases is firstly collected through the machine olfactory system and then analyzed through a Selected Linear Discriminate Analysis (SLDA) combined with a Markov two-dimensional distance discriminant method to identify various toxic and harmful gases. The algorithm disclosed in the invention extracts the characteristic information of the sample data, and then fast processes and identifies the information as a linear recognition algorithm does, having wide applications in the field of machine olfaction, especially in detecting and identifying the toxic and harmful gases in real-time based on machine olfaction. The algorithm involves low complexity and high recognition efficiency.

5 Claims, 5 Drawing Sheets

(58) Field of Classification Search
CPC ......... G01N 2291/0256; G01N 29/022; G01N 21/3504; G01N 2291/0217; G01N 33/004; G05B 23/0254; G05B 19/042; G06F 17/16
USPC ....... 73/1.02, 23.1, 23.2, 23.3, 23.34, 31.05; 340/517, 539.22, 603, 632; 382/128; 422/68.1, 83; 700/28, 49; 702/24, 19, 702/22, 32, 30, 188, 31, 189, 1, 85; 703/6, 11; 706/1, 45–46
See application file for complete search history.

(56) References Cited

U.S. PATENT DOCUMENTS

| | | | |
|---|---|---|---|
| 2001/0027678 A1* | 10/2001 | Mottram | G01N 33/0031 73/23.2 |
| 2004/0006257 A1* | 1/2004 | Burch | A61B 5/00 600/300 |
| 2004/0181346 A1* | 9/2004 | Sunshine | H04L 29/06 702/22 |
| 2009/0261987 A1* | 10/2009 | Sun | G01N 33/0075 340/870.07 |
| 2016/0061761 A1* | 3/2016 | Shim | G01N 27/122 436/151 |
| 2018/0011066 A1* | 1/2018 | Loubet | G01N 33/0047 |

FOREIGN PATENT DOCUMENTS

| | | |
|---|---|---|
| CN | 104102818 A | 10/2014 |
| CN | 105954412 A | 9/2016 |

\* cited by examiner

Classify gas samples into K types each having N gas samples; select and save data from rows 55-69 of $S_{data1}$ as $S_{ij}$; and calculate a mean matrix μ of each column of $S_{ij}$ Obtain mean matrices μ of $S_{ij}$ of all gas samples to form a matrix P of all gas samples, $p=\{x_1^n, x_2^n, ... x_k^n\}$ 1) Calculate a mean matrix $\mu_j$ of $x_k^N$ of each type of gas samples 2) Calculate a mean matrix $\mu_k$ of the matrix P of all gas samples 3) Calculate a within-class scatter matrix $J_W$ and a between-class scatter matrix $J_B$ of the matrix P of all gas samples 4) Calculate an objective optimization function $\emptyset(\omega)$ of the matrix P, $\emptyset(\omega) = \dfrac{\omega J_B \omega^T}{\omega J_W \omega^T}$, and calculate an eigenvalue $\lambda$ Calculate a recognition feature matrix $M_{train}$ according to $M_{train} = P \times \lambda$

FIG. 2

Step (1): Set a recognition feature matrix of each type of trained gas samples as $M_{traink}$, and calculate mean matrix $A_{traink}$ for all columns of $M_{traink}$ according to $A_{traink} = \sum_{i=1}^{N} M_{traink}$ extract the first two columns of $A_{traink}$ to obtain $A_{traink12}$, $A_{traink12} = (x_{i1}, x_{i2})$ Step (2): Select the first two columns of $M_{test}$ to obtain $A_{traink12}$, $A_{traink12} = (x_{j1}, x_{j2})$ Step (3): Calculate two-dimensional spatial distance d of $A_{traink12}$ and $A_{testk12}$, $d = \sqrt{(x_{j1} - x_{i1})^2 + (x_{j2} - x_{i2})^2}$

FIG. 3

METHOD FOR DETECTING AND IDENTIFYING TOXIC AND HARMFUL GASES BASED ON MACHINE OLFACTION

CROSS-REFERENCE TO RELATED APPLICATIONS

This application is a continuation of International Patent Application No. PCT/CN2017/107087, filed on Oct. 20, 2017, which claims the benefit of priority from Chinese Application No. 201710785985.7, filed on Aug. 30, 2017. The content of the aforementioned applications, including any intervening amendments thereto, are incorporated herein by reference.

TECHNICAL FIELD

The present application relates to gas detection and identification, and more particularly to a method for detecting and identifying toxic and harmful gases based on machine olfaction.

BACKGROUND OF THE INVENTION

Gas leak often occurs in industrial processes and leads to serious hazard to persons and property when leaked gas is toxic, harmful, flammable and explosive gases. For example, on 12 Aug. 2015, a series of explosions occurred in Binhai New Area of Tianjin, China; and on 21 Jul. 2017, gas blast occurred in West Lack District of Hangzhou, China, Therefore, it is of great significance to develop a method for timely detecting and identifying toxic, harmful, flammable and explosive gases.

Currently, toxic and harmful gases are detected mainly through PH test paper method, photochemical method, as well as devices such as gas chromatographs, gas sensors and related instruments.

Gao Daqi et al. disclosed "Small-scale automated machine olfactory device and odor analysis method" (Chinese Patent ZL200710036260.4), where the machine olfactory device includes a test box, a thermostatic cup, an automatic sampling lifting device, a computer, a display device, and an oxygen cylinder. The odor analysis method involves the use of head-space sampling manner and 16 gas sensors. 4 thermostatic cups are provided in the machine olfactory device to achieve continuous measurement.

Li Taixi et al. disclosed "Device and method for judging odor perception" (Chinese Patent Application No. 201510784670.1), where the sensor array includes two or more sensors which are capable of detecting VOCs, $H_2S$, $NH_3$, $H_2$, EtOH, trimethylamine, ethanol, solvent vapor, methane, COCFC's, $CO_2$, $O_3$, $NO_2$, etc.

These methods list several detection means, but they fail to describe a specific gas detection method and the related process. Therefore, there is an urgent need to realize the real-time detection and identification of toxic and harmful gases.

SUMMARY OF THE INVENTION

This invention provides a method for detecting and identifying toxic and harmful gases based on machine olfaction to overcome at least one of the drawbacks in the prior art. Information about the toxic and harmful gases is collected through a machine olfactory system and analyzed through a Selected Linear Discriminate Analysis (SLDA) combined with a two-dimensional distance discriminant method to construct an odor information base, thereby identifying various toxic and harmful gases.

The technical solution of the invention is described as follows.

A method for detecting and identifying toxic and harmful gases based on machine olfaction, comprising:

(1) collecting and storing a gas sample in a sampling bag through an electric air pump, and delivering the gas sample in the sampling bag via a gas valve to a gas chamber provided in a constant temperature and humidity device;

(2) delivering the gas sample to a sensor chamber through a hole of the sampling bag to contact a sensor array to obtain measurement data; performing A/D conversion on the measurement data through an A/D acquisition card; transferring the converted data to a computer and saving the data as $S_{data}$;

(3) performing data feature extraction on the collected data $S_{data}$, and obtaining a recognition feature matrix $M_{train}$ through a selected linear discriminate analysis; and (4) repeating steps (1)-(3) to obtain a recognition feature matrix $M_{test}$ of a gas sample; and comparing $M_{test}$ and $M_{train}$ by using a two-dimensional distance discriminant method to identify the type of the gas sample.

In some embodiments, in step (1), a hole diameter of the gas valve is 5 mm; a volume of the sampling bag is 600 ml; a volume of the gas chamber is 600 ml; the gas is delivered to the gas chamber at a flow rate of 5 ml/s; the constant temperature and humidity device is Type ZH-TH-80 with an internal dimension of 400×500×400 mm and an external dimension of 1050×1650×980 mm, and is set with a temperature of 30° C., and a relative humidity of 50-60%.

In some embodiments, in step (2), the sensor array consists of 10 metal oxide gas sensors which are uniformly arranged in a circle with a diameter of 10.2 cm; a gas sampling time is 120 s; and the A/D acquisition card is Type AD7705.

In some embodiments, the selected linear discriminate analysis in step (3) comprises the following steps:

(1) classifying gas samples into K types each having N gas samples; setting the collected and measured data of single gas sample as $S_{data1}$, wherein $S_{data1} \in R^{120 \times 10}$, and $S_{data1}$ has 120 rows and 10 columns; selecting and saving data from rows 55-69 of $S_{data1}$ as $S_{ij}$, wherein $S_{ij} \in R^{15 \times 10}$, and $S_{ij}$ has 15 rows and 10 columns; calculating a mathematical characteristic, a mean matrix $\mu$ for each column of $S_{ij}$ of the single gas sample according to the following equation;

$$\mu = \frac{1}{q}\Sigma S_{ij}, \mu \in R^{1 \times 10} \qquad (1)$$

wherein q is the number of rows of $S_{ij}$ of the single gas sample, and q=15;

(2) obtaining mean matrices $\mu$ of $S_{ij}$ of all gas samples according to step (1) to form a matrix P of all gas samples, wherein $P=\{X_1^N, X_2^N, \Lambda X_k^N\}$; $X_k^N \in R^{N \times 10}$, and $X_k^N$ has N rows and 10 columns; $P \in R^{M \cdot N \times 10}$, and the matrix P has M·N rows and 10 columns;

calculating a mathematical characteristic, a mean matrix $\mu_j$ for columns of $X_k^N$ of a single type of gas samples according to the following equation:

$$\mu_j = \frac{1}{N}\Sigma\mu, \mu_j \in R^{K \times 10}, N \in [1, N] \qquad (2)$$

then calculating a mean matrix $\mu_k$ of the matrix P of all gas samples according to the following equation;

$$\mu_k = \frac{1}{K}\Sigma\mu_j, \mu_k \in R^{1\times10}, K \in [1, K] \qquad (3)$$

then calculating a within-class scatter matrix $J_W$ and a between-class scatter matrix $J_B$ of the matrix P of all gas samples according to the following equations;

$$J_W = \sum_{N=1}^{N}\sum_{K=1}^{K}(\mu_j - X_K^N)^T(\mu_j - X_K^N), J_W \in R^{10\times10} \qquad (4)$$

$$J_B = \sum_{K=1}^{K}(\mu_K - \mu_j)^T(\mu_K - \mu_j), J_B \in R^{10\times10} \qquad (5)$$

and calculating an objective optimization function $\phi(\omega)$ of the matrix P,
wherein $\phi(\omega)$ is expressed as $$\phi(\omega) = \frac{\omega J_B \omega^T}{\omega J_W \omega^T} \qquad (6)$$

when $\phi(\omega)$ takes the maximum value, the eigenvalue $\omega$ satisfies a maximum $J_B$ value and a minimum $J_W$ value, so that conditions for the optimization of the matrix P are satisfied;
setting the eigenvalue as $\lambda$, plugging $\omega J_W \omega^T = 1$ into the equation (6), as shown in formula (7), $$\begin{cases} \phi(\omega) = \frac{\omega J_B \omega^T}{\omega J_W \omega^T} \\ \omega J_W \omega^T = 1 \end{cases} \qquad (7)$$

thus converting the equation (6) by Lagrange multiplier method to obtain the following equation:

$$\phi(\omega)' = \omega J_B \omega^T - \lambda(\omega J_W \omega^T - 1) \qquad (8)$$

performing derivation on $\omega$ on both sides of the equation (8) to solve the eigenvalue of the matrix formed from $J_B$ and $J_W$, as shown in the following equation:

$$\frac{d\phi(\omega)'}{d\omega} = 2J_B\omega - 2\lambda J_W\omega = 0 \qquad (9)$$

to obtain $\lambda = J_B J_W^{-1}, \lambda \in R^{10\times10}$; (10)

and
(3) calculating a recognition feature matrix $M_{train}$ according to the following equation:

$$M_{train} = P\times\lambda, M_{train} \in R^{M\cdot N\times10} \qquad (11)$$

In some embodiments, the two-dimensional distance discriminant method in step (4) comprises the following steps:
(1) setting a recognition feature matrix of trained gas samples as $M_{train}$, and setting a recognition feature matrix of each type of trained gas samples as $M_{traink}$, and calculating a mean matrix $A_{traink}$ for all columns of $M_{traink}$ according to the following equation:

$$A_{traink} = \sum_{i=1}^{N} M_{traink}, A_{traink} \in R^{1\times10} \qquad (12)$$

extracting the first two columns of $A_{traink}$ to obtain $A_{traink12}$ which is expressed as $$A_{traink12} = (x_{i1}, x_{i2}) \qquad (13);$$

(2) setting a recognition feature matrix of gas samples to be tested as $M_{test}$, and extracting the first two columns of $M_{test}$ as $A_{testk12}$, which is expressed as:

$$A_{testk12} = (x_{j1}, x_{j2}) \qquad (14);$$

and
(3) calculating a two-dimensional spatial distance d of $A_{traink12}$ and $A_{testk12}$ according to the following equation:

$$d = \sqrt{(x_{j1}-x_{i1})^2 + (x_{j2}-x_{i2})^2} \qquad (15);$$

wherein d being close to 0 indicates a close spatial distance, indicating that the gas sample to be tested and the trained gas sample are identified as the same type of gas.

Compared with the prior art, the invention has the following beneficial effects.

This invention provides a method for detecting and identifying toxic and harmful gases based on machine olfactory, where the information about the toxic and harmful gases is collected through the machine olfactory system and analyzed through the Selected Linear Discriminate Analysis (SLDA) combined with the Markov two-dimensional distance discriminant method to identify various toxic and harmful gases. The algorithm disclosed in the invention extracts the characteristic information of the sample data, and then fast processes and identifies the information as a linear recognition algorithm does, having wide applications in the field of machine olfaction, especially in detecting and identifying the toxic and harmful gases in real-time based on machine olfaction. The algorithm involves low complexity and high recognition efficiency.

BRIEF DESCRIPTION OF THE DRAWINGS

FIG. 2 is a flowchart of a selected linear discriminate analysis algorithm.
FIG. 3 is a flow chart of a two-dimensional distance discriminant method.

DETAILED DESCRIPTION OF EMBODIMENTS

Figure 1:
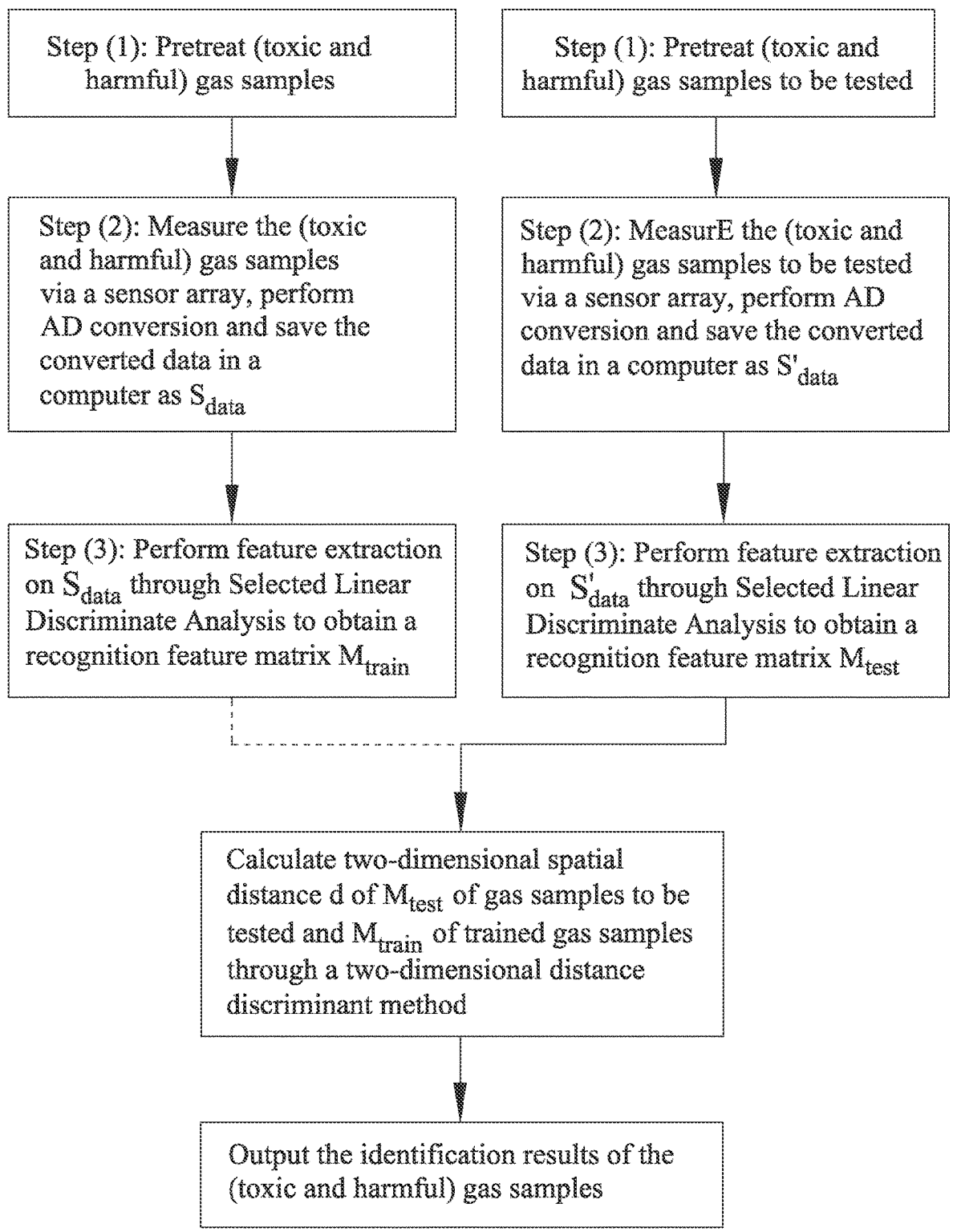
FIG. 1 is a flowchart of detecting and identifying toxic and harmful gases based on machine olfaction of the present invention.

The accompanying drawings are only for illustration and are not intended to limit the present invention;
In order to better illustrate the embodiments, some components in the drawings may be omitted, enlarged or reduced, and do not present the actual size of the product.
It will be understood by those skilled in the art that some well-known structures in the drawings and the descriptions thereof may be omitted.
The technical solution of the present invention will be further described below with reference to the accompanying drawings and embodiments.

Example 1

Common toxic and harmful gases such as $CO_2$, $CH_4$, $NH_3$ and VOCs were measured and identified in this embodiment. Each of these 4 types gases had 20 samples, among these 20 samples, 10 samples were chosen for training, and 2 samples were randomly chosen for the measurement. A method for detecting and identifying toxic and harmful gases based on machine olfaction included the following steps, as shown in FIG. 1.

(1) 4 types of gas samples were collected and stored in a 600 ml gas sampling bag through an electric air pump, and then delivered to a gas chamber via a gas valve at a flow rate of 5 ml/s, where a hole diameter of the gas valve is 5 mm; a volume of the gas chamber is 600 ml, and the gas chamber was provided in a constant temperature and humidity device which was Type ZH-TH-80 with an internal dimension of 400×500×400 mm and an external dimension of 1050×1650×980 mm. The constant temperature and humidity device was set with a temperature of 30° C., and a relative humidity of 50-60%.

(2) The 4 types of gas samples passed through a hole of the gas sampling bag and entered into a sensor chamber to contact a sensor array and obtain measurement data. The sensor array consisted of 10 metal oxide gas sensors which were uniformly arranged in a circle with a diameter of 10.2 cm. A gas sampling time was 120 s. A/D conversion was performed on the measurement data through an A/D acquisition card which was Type AD7705. The converted data were transferred to a computer and saved as $S_{data}$.

(3) Data feature extraction was performed on the collected data $S_{data}$, and then a recognition feature matrix $M_{train}$ was obtained through a selected linear discriminate analysis (SLDA).

In this embodiment, the selected linear discriminate analysis in Step (3) further included the following steps.

(1) 4 types of gas samples including $CO_2$, $CH_4$, $NH_3$ and VOCs were collected, and each type had 10 gas samples. A single gas sample was randomly chosen among the 10 gas samples and was measured to obtain data $S_{data1}$, where $S_{data1} \in R^{120 \times 10}$, and $S_{data1}$ had 120 rows and 10 columns, as shown in Table 1.

TABLE 1

$S_{data1}$ of the randomly selected gas sample

| No. | 1 | 2 | 3 | 4 | 5 | 6 | 7 | 8 | 9 | 10 |
|---|---|---|---|---|---|---|---|---|---|---|
| 1 | 0.9604 | 0.9965 | 0.9736 | 0.9942 | 0.9694 | 1 | 0.9599 | 0.9984 | 0.9629 | 0.9962 |
| 2 | 1.0234 | 0.997 | 1.0223 | 0.9959 | 1.0193 | 1.0026 | 1.0008 | 0.9984 | 0.9901 | 0.9976 |
| 3 | 1.0438 | 1.0048 | 1.0296 | 1 | 1.0343 | 1.0099 | 1.0227 | 1.0021 | 1.0119 | 1.0015 |
| 4 | 0.9985 | 1.046 | 0.9965 | 1.001 | 0.9985 | 1.0447 | 1.0054 | 1.0277 | 1.0044 | 1.0003 |
| 5 | 0.9802 | 1.1038 | 0.9822 | 1.0041 | 0.9835 | 1.0869 | 1.0001 | 1.0597 | 1.0037 | 0.9976 |
| 6 | 0.9692 | 1.1525 | 0.972 | 1.0074 | 0.9746 | 1.1244 | 1.001 | 1.0908 | 1.005 | 0.9969 |
| 7 | 0.9591 | 1.1924 | 0.9622 | 1.0124 | 0.9675 | 1.1583 | 1.0036 | 1.1176 | 1.0062 | 0.9958 |
| 8 | 0.9483 | 1.2244 | 0.9523 | 1.0169 | 0.9596 | 1.1878 | 1.0046 | 1.142 | 1.0096 | 0.9945 |
| 9 | 0.9372 | 1.2496 | 0.9428 | 1.0216 | 0.9525 | 1.2128 | 1.0056 | 1.1647 | 1.0119 | 0.9937 |
| 10 | 0.9274 | 1.2702 | 0.9338 | 1.024 | 0.9459 | 1.2356 | 1.0065 | 1.1833 | 1.016 | 0.9926 |
| 11 | 0.9175 | 1.2874 | 0.9265 | 1.0278 | 0.9397 | 1.2548 | 1.009 | 1.204 | 1.0185 | 0.9927 |
| 12 | 0.9086 | 1.3001 | 0.9183 | 1.0312 | 0.9333 | 1.2722 | 1.0105 | 1.2185 | 1.0209 | 0.9928 |
| 13 | 0.9003 | 1.3131 | 0.9104 | 1.0349 | 0.9274 | 1.2859 | 1.012 | 1.2326 | 1.0247 | 0.9912 |
| 14 | 0.892 | 1.3218 | 0.9038 | 1.0382 | 0.9227 | 1.2996 | 1.0147 | 1.245 | 1.029 | 0.9925 |
| 15 | 0.8847 | 1.3278 | 0.8976 | 1.0413 | 0.9173 | 1.311 | 1.0152 | 1.2586 | 1.031 | 0.9922 |
| 16 | 0.8781 | 1.3359 | 0.8913 | 1.0447 | 0.9129 | 1.3207 | 1.0154 | 1.2688 | 1.0336 | 0.9921 |
| 17 | 0.8703 | 1.3402 | 0.8854 | 1.0461 | 0.9096 | 1.3302 | 1.0182 | 1.2805 | 1.0361 | 0.9902 |
| 18 | 0.8657 | 1.3449 | 0.8796 | 1.0482 | 0.9044 | 1.3358 | 1.0196 | 1.2891 | 1.0396 | 0.9912 |
| 19 | 0.8588 | 1.3505 | 0.8748 | 1.051 | 0.9009 | 1.3432 | 1.0206 | 1.2977 | 1.0417 | 0.9912 |
| 20 | 0.8532 | 1.3549 | 0.8699 | 1.0523 | 0.8971 | 1.3505 | 1.0206 | 1.3066 | 1.0453 | 0.9911 |
| 21 | 0.848 | 1.3588 | 0.8646 | 1.0559 | 0.8936 | 1.3574 | 1.0211 | 1.3109 | 1.0487 | 0.9904 |
| 22 | 0.8424 | 1.36 | 0.8607 | 1.0582 | 0.8902 | 1.3589 | 1.0226 | 1.3161 | 1.0507 | 0.9914 |
| 23 | 0.8381 | 1.361 | 0.8571 | 1.0595 | 0.8871 | 1.3623 | 1.024 | 1.3227 | 1.0555 | 0.9918 |
| 24 | 0.8337 | 1.3612 | 0.8529 | 1.0628 | 0.8837 | 1.3665 | 1.0253 | 1.3282 | 1.0575 | 0.9918 |
| 25 | 0.8292 | 1.3629 | 0.8491 | 1.0632 | 0.8817 | 1.3699 | 1.0261 | 1.3328 | 1.059 | 0.9921 |
| 26 | 0.8251 | 1.3644 | 0.8455 | 1.0663 | 0.8786 | 1.3722 | 1.0271 | 1.3383 | 1.0623 | 0.9915 |
| 27 | 0.8219 | 1.3644 | 0.8426 | 1.0685 | 0.8758 | 1.3759 | 1.0294 | 1.3418 | 1.0653 | 0.9914 |
| 28 | 0.8184 | 1.3661 | 0.8386 | 1.0691 | 0.8735 | 1.3773 | 1.0301 | 1.3484 | 1.0685 | 0.9914 |
| 29 | 0.8144 | 1.3666 | 0.8358 | 1.0693 | 0.8709 | 1.3788 | 1.031 | 1.3513 | 1.0713 | 0.9927 |
| 30 | 0.8111 | 1.3673 | 0.8327 | 1.0703 | 0.8692 | 1.3795 | 1.031 | 1.3528 | 1.074 | 0.992 |
| 31 | 0.8083 | 1.3681 | 0.8302 | 1.0716 | 0.8676 | 1.3816 | 1.0348 | 1.3536 | 1.076 | 0.9917 |
| 32 | 0.8057 | 1.3688 | 0.8277 | 1.0728 | 0.8648 | 1.3836 | 1.0359 | 1.3542 | 1.0809 | 0.9924 |
| 33 | 0.8028 | 1.3661 | 0.8248 | 1.0741 | 0.8627 | 1.3843 | 1.0362 | 1.3577 | 1.0842 | 0.9912 |
| 34 | 0.7993 | 1.3676 | 0.8226 | 1.0755 | 0.8613 | 1.3847 | 1.0385 | 1.3592 | 1.0847 | 0.9921 |
| 35 | 0.7958 | 1.3676 | 0.8198 | 1.0765 | 0.8593 | 1.3855 | 1.0397 | 1.3618 | 1.0869 | 0.9911 |
| 36 | 0.7937 | 1.3661 | 0.8187 | 1.0786 | 0.8577 | 1.3855 | 1.0409 | 1.3618 | 1.0886 | 0.9921 |
| 37 | 0.7923 | 1.3666 | 0.8163 | 1.0793 | 0.8561 | 1.3857 | 1.0414 | 1.3644 | 1.0919 | 0.9922 |
| 38 | 0.7902 | 1.3666 | 0.8145 | 1.0804 | 0.8553 | 1.3854 | 1.0414 | 1.3644 | 1.0951 | 0.9922 |
| 39 | 0.7882 | 1.3661 | 0.8122 | 1.0808 | 0.8535 | 1.3857 | 1.0423 | 1.3676 | 1.0978 | 0.9927 |
| 40 | 0.7858 | 1.3659 | 0.8101 | 1.0816 | 0.8521 | 1.3854 | 1.0434 | 1.3685 | 1.1 | 0.9922 |
| 41 | 0.7842 | 1.3661 | 0.8082 | 1.0837 | 0.8504 | 1.3854 | 1.0446 | 1.3702 | 1.1019 | 0.9926 |
| 42 | 0.7817 | 1.3654 | 0.8071 | 1.0856 | 0.8493 | 1.3854 | 1.046 | 1.3717 | 1.1046 | 0.9932 |
| 43 | 0.7803 | 1.3654 | 0.8052 | 1.0863 | 0.8481 | 1.3848 | 1.0468 | 1.3705 | 1.1085 | 0.9925 |
| 44 | 0.779 | 1.3654 | 0.804 | 1.0866 | 0.8468 | 1.3843 | 1.0474 | 1.372 | 1.1112 | 0.9933 |
| 45 | 0.7776 | 1.3629 | 0.8021 | 1.0871 | 0.8455 | 1.384 | 1.0488 | 1.3726 | 1.1115 | 0.9933 |
| 46 | 0.7758 | 1.3632 | 0.8009 | 1.0878 | 0.8445 | 1.3836 | 1.0503 | 1.3737 | 1.1138 | 0.9943 |
| 47 | 0.7744 | 1.362 | 0.7995 | 1.0874 | 0.8433 | 1.3826 | 1.0514 | 1.3737 | 1.1165 | 0.9927 |
| 48 | 0.7721 | 1.3615 | 0.798 | 1.0898 | 0.8429 | 1.3826 | 1.0526 | 1.3746 | 1.1188 | 0.9932 |
| 49 | 0.771 | 1.3612 | 0.7967 | 1.0905 | 0.8424 | 1.3821 | 1.0543 | 1.3737 | 1.1209 | 0.9933 |

TABLE 1-continued $S_{data}$ of the randomly selected gas sample

| No. | 1 | 2 | 3 | 4 | 5 | 6 | 7 | 8 | 9 | 10 |
|---|---|---|---|---|---|---|---|---|---|---|
| 50 | 0.7695 | 1.3615 | 0.7957 | 1.0914 | 0.8418 | 1.3788 | 1.0553 | 1.3746 | 1.1233 | 0.993 |
| 51 | 0.7684 | 1.3612 | 0.7943 | 1.0922 | 0.8407 | 1.379 | 1.0565 | 1.3752 | 1.126 | 0.9935 |
| 52 | 0.7675 | 1.361 | 0.793 | 1.0923 | 0.8392 | 1.3787 | 1.0572 | 1.3761 | 1.1279 | 0.9935 |
| 53 | 0.7657 | 1.3602 | 0.7917 | 1.0923 | 0.8384 | 1.3783 | 1.058 | 1.3758 | 1.1303 | 0.9925 |
| 54 | 0.765 | 1.3605 | 0.7909 | 1.0928 | 0.8374 | 1.3783 | 1.0597 | 1.3761 | 1.1339 | 0.9927 |
| 55 | 0.6297 | 1.6385 | 0.6308 | 1.0711 | 0.6822 | 1.9925 | 1.0298 | 2.049 | 1.1954 | 0.9899 |
| 56 | 0.6297 | 1.6363 | 0.6303 | 1.0716 | 0.682 | 1.9891 | 1.0304 | 2.049 | 1.1994 | 0.9892 |
| 57 | 0.6296 | 1.6342 | 0.6298 | 1.0723 | 0.6815 | 1.9875 | 1.0307 | 2.0451 | 1.2009 | 0.9904 |
| 58 | 0.6283 | 1.6297 | 0.6292 | 1.072 | 0.6814 | 1.986 | 1.0308 | 2.0444 | 1.2021 | 0.9895 |
| 59 | 0.628 | 1.6284 | 0.6293 | 1.0737 | 0.681 | 1.9823 | 1.0313 | 2.0415 | 1.2046 | 0.99 |
| 60 | 0.6276 | 1.6253 | 0.6289 | 1.0732 | 0.6812 | 1.9797 | 1.0316 | 2.0402 | 1.2073 | 0.9886 |
| 61 | 0.6277 | 1.6238 | 0.6293 | 1.0744 | 0.6806 | 1.9759 | 1.0317 | 2.0373 | 1.2095 | 0.9902 |
| 62 | 0.6277 | 1.621 | 0.6292 | 1.0746 | 0.6802 | 1.9721 | 1.0321 | 2.034 | 1.2112 | 0.9902 |
| 63 | 0.6276 | 1.62 | 0.6291 | 1.0749 | 0.6801 | 1.9691 | 1.0324 | 2.0321 | 1.2148 | 0.9906 |
| 64 | 0.6274 | 1.6178 | 0.6291 | 1.0752 | 0.6798 | 1.9651 | 1.0328 | 2.0282 | 1.217 | 0.9902 |
| 65 | 0.627 | 1.6165 | 0.629 | 1.0758 | 0.6801 | 1.9623 | 1.0329 | 2.0269 | 1.2193 | 0.9902 |
| 66 | 0.6274 | 1.6142 | 0.6294 | 1.0758 | 0.6794 | 1.9583 | 1.0334 | 2.0218 | 1.221 | 0.9914 |
| 67 | 0.6271 | 1.6089 | 0.629 | 1.0758 | 0.68 | 1.9545 | 1.0344 | 2.0211 | 1.225 | 0.9909 |
| 68 | 0.6273 | 1.6082 | 0.6292 | 1.0762 | 0.6797 | 1.9506 | 1.0349 | 2.0188 | 1.2254 | 0.9915 |
| 69 | 0.6269 | 1.6032 | 0.6292 | 1.0759 | 0.6796 | 1.9485 | 1.035 | 2.0179 | 1.227 | 0.9907 |
| 70 | 0.7514 | 1.35 | 0.7795 | 1.0976 | 0.8286 | 1.3616 | 1.0739 | 1.3723 | 1.166 | 0.9937 |
| 71 | 0.7513 | 1.3497 | 0.7787 | 1.0986 | 0.8282 | 1.3601 | 1.0758 | 1.3732 | 1.1669 | 0.9932 |
| 72 | 0.7505 | 1.3505 | 0.7781 | 1.0988 | 0.8267 | 1.3592 | 1.0769 | 1.3729 | 1.1682 | 0.9944 |
| 73 | 0.7505 | 1.3497 | 0.7778 | 1.0988 | 0.8267 | 1.3584 | 1.0777 | 1.372 | 1.1701 | 0.9944 |
| 74 | 0.7501 | 1.3475 | 0.7774 | 1.098 | 0.8263 | 1.3586 | 1.0782 | 1.3714 | 1.1727 | 0.9928 |
| 75 | 0.7502 | 1.347 | 0.7774 | 1.0994 | 0.8259 | 1.3584 | 1.0788 | 1.3705 | 1.1734 | 0.9937 |
| 76 | 0.749 | 1.3463 | 0.7768 | 1.0995 | 0.8256 | 1.3574 | 1.0802 | 1.3697 | 1.1759 | 0.9933 |
| 77 | 0.7475 | 1.3458 | 0.7764 | 1.1003 | 0.825 | 1.3572 | 1.0822 | 1.3691 | 1.1776 | 0.9934 |
| 78 | 0.7475 | 1.3456 | 0.7756 | 1.1004 | 0.8242 | 1.3548 | 1.0826 | 1.3673 | 1.1792 | 0.9935 |
| 79 | 0.7473 | 1.3446 | 0.7757 | 1.1004 | 0.824 | 1.3532 | 1.0836 | 1.367 | 1.1809 | 0.994 |
| 80 | 0.7473 | 1.3446 | 0.7754 | 1.006 | 0.8241 | 1.3513 | 1.0834 | 1.3679 | 1.183 | 0.9944 |
| 81 | 0.7467 | 1.3417 | 0.7748 | 1.101 | 0.8236 | 1.3506 | 1.0842 | 1.3656 | 1.1849 | 0.9938 |
| 82 | 0.7467 | 1.3414 | 0.7749 | 1.1016 | 0.8236 | 1.3498 | 1.0841 | 1.3644 | 1.1866 | 0.9937 |
| 83 | 0.7464 | 1.3412 | 0.774 | 1.1022 | 0.8236 | 1.3489 | 1.0853 | 1.3641 | 1.1891 | 0.993 |
| 84 | 0.7464 | 1.34 | 0.7741 | 1.103 | 0.8235 | 1.3467 | 1.0864 | 1.3627 | 1.1903 | 0.994 |
| 85 | 0.7452 | 1.3405 | 0.7736 | 1.1025 | 0.8235 | 1.3454 | 1.0873 | 1.3632 | 1.1934 | 0.9933 |
| 86 | 0.746 | 1.3405 | 0.7732 | 1.103 | 0.8232 | 1.3444 | 1.0881 | 1.3624 | 1.1938 | 0.9938 |
| 87 | 0.7451 | 1.3395 | 0.7729 | 1.1033 | 0.8227 | 1.3441 | 1.0893 | 1.3606 | 1.1938 | 0.9934 |
| 88 | 0.7435 | 1.3397 | 0.7735 | 1.1036 | 0.8228 | 1.3429 | 1.0897 | 1.3603 | 1.1948 | 0.9941 |
| 89 | 0.7437 | 1.3397 | 0.7723 | 1.1036 | 0.8225 | 1.3414 | 1.0904 | 1.3606 | 1.1969 | 0.9937 |
| 90 | 0.7432 | 1.3385 | 0.7719 | 1.1041 | 0.8224 | 1.3399 | 1.0913 | 1.3595 | 1.1985 | 0.9939 |
| 91 | 0.743 | 1.3376 | 0.7716 | 1.1039 | 0.8217 | 1.34 | 1.0927 | 1.3597 | 1.2006 | 0.993 |
| 92 | 0.743 | 1.3371 | 0.772 | 1.1042 | 0.8213 | 1.3382 | 1.0935 | 1.3577 | 1.2027 | 0.9944 |
| 93 | 0.7429 | 1.3361 | 0.7712 | 1.1042 | 0.8213 | 1.3375 | 1.0944 | 1.3568 | 1.2039 | 0.9931 |
| 94 | 0.7424 | 1.3351 | 0.7711 | 1.1041 | 0.8209 | 1.3365 | 1.0951 | 1.3568 | 1.2053 | 0.9938 |
| 95 | 0.7423 | 1.3351 | 0.771 | 1.1041 | 0.8209 | 1.3347 | 1.0963 | 1.3545 | 1.2072 | 0.9937 |
| 96 | 0.7419 | 1.3351 | 0.771 | 1.1044 | 0.8207 | 1.3335 | 1.0982 | 1.3545 | 1.2083 | 0.9935 |
| 97 | 0.7416 | 1.3337 | 0.7704 | 1.1045 | 0.8206 | 1.3322 | 1.0978 | 1.3545 | 1.2106 | 0.9937 |
| 98 | 0.7416 | 1.3332 | 0.7703 | 1.1045 | 0.8203 | 1.3318 | 1.0988 | 1.3539 | 1.212 | 0.9948 |
| 99 | 0.742 | 1.3317 | 0.77 | 1.1044 | 0.8203 | 1.3317 | 1.0998 | 1.3542 | 1.2134 | 0.9932 |
| 100 | 0.7413 | 1.3315 | 0.7702 | 1.1051 | 0.8201 | 1.3315 | 1.1005 | 1.3534 | 1.2146 | 0.9941 |
| 101 | 0.7404 | 1.3305 | 0.7699 | 1.1051 | 0.8201 | 1.3315 | 1.1013 | 1.3534 | 1.2162 | 0.9939 |
| 102 | 0.7402 | 1.33 | 0.7705 | 1.1048 | 0.8199 | 1.3315 | 1.1033 | 1.3531 | 1.2169 | 0.9945 |
| 103 | 0.7401 | 1.3298 | 0.77 | 1.1053 | 0.8198 | 1.3305 | 1.1036 | 1.3531 | 1.2192 | 0.9939 |
| 104 | 0.7407 | 1.3281 | 0.7695 | 1.1057 | 0.8194 | 1.33 | 1.1042 | 1.3528 | 1.2218 | 0.9933 |
| 105 | 0.74 | 1.3278 | 0.7694 | 1.1057 | 0.8195 | 1.3297 | 1.105 | 1.3531 | 1.2218 | 0.9937 |
| 106 | 0.7399 | 1.3293 | 0.7694 | 1.106 | 0.8191 | 1.3278 | 1.1052 | 1.3522 | 1.2222 | 0.9943 |
| 107 | 0.7398 | 1.3295 | 0.7696 | 1.106 | 0.8189 | 1.3273 | 1.1054 | 1.3522 | 1.2232 | 0.9944 |
| 108 | 0.7397 | 1.3303 | 0.768 | 1.1077 | 0.8192 | 1.3254 | 1.1054 | 1.3525 | 1.2252 | 0.9926 |
| 109 | 0.74 | 1.3295 | 0.7687 | 1.1065 | 0.8183 | 1.3247 | 1.1065 | 1.3525 | 1.2259 | 0.9941 |
| 110 | 0.7397 | 1.3286 | 0.7685 | 1.1072 | 0.8181 | 1.3249 | 1.1068 | 1.3519 | 1.2264 | 0.994 |
| 111 | 0.7392 | 1.3286 | 0.7687 | 1.1075 | 0.818 | 1.3247 | 1.1072 | 1.3513 | 1.2284 | 0.9938 |
| 112 | 0.7394 | 1.3283 | 0.7682 | 1.1081 | 0.8181 | 1.3234 | 1.108 | 1.3513 | 1.2299 | 0.9939 |
| 113 | 0.7391 | 1.3286 | 0.7676 | 1.1092 | 0.818 | 1.3229 | 1.109 | 1.3505 | 1.2317 | 0.9938 |
| 114 | 0.7385 | 1.3264 | 0.768 | 1.1092 | 0.8183 | 1.3229 | 1.11 | 1.3507 | 1.2333 | 0.9933 |
| 115 | 0.7388 | 1.3266 | 0.768 | 1.1083 | 0.8181 | 1.3199 | 1.1111 | 1.3502 | 1.2344 | 0.9933 |
| 116 | 0.7387 | 1.3257 | 0.7683 | 1.1092 | 0.8177 | 1.3186 | 1.1117 | 1.3432 | 1.2356 | 0.9943 |
| 117 | 0.7387 | 1.3257 | 0.7675 | 1.1092 | 0.8177 | 1.3166 | 1.1122 | 1.3473 | 1.237 | 0.994 |
| 118 | 0.7387 | 1.3245 | 0.7678 | 1.1095 | 0.8176 | 1.3164 | 1.1126 | 1.3449 | 1.2386 | 0.9935 |
| 119 | 0.7384 | 1.3232 | 0.7676 | 1.1096 | 0.8176 | 1.3143 | 1.1138 | 1.3426 | 1.2386 | 0.9934 |
| 120 | 0.7379 | 1.323 | 0.7678 | 1.1086 | 0.8177 | 1.3136 | 1.1148 | 1.3415 | 1.24 | 0.9935 |

Firstly, data from rows 55-69 of $S_{data1}$ were selected and saved as $S_{ij}$, where $S_{ij} \in R^{15 \times 10}$, and $S_{ij}$ had 15 rows and 10 columns, as shown in Table 2.

TABLE 2

Feature data $S_{ij}$ of the randomly selected gas sample (rows 55-69)

| No. | 1 | 2 | 3 | 4 | 5 | 6 | 7 | 8 | 9 | 10 |
|---|---|---|---|---|---|---|---|---|---|---|
| 55 | 0.6297 | 1.6385 | 0.6308 | 1.0711 | 0.6822 | 1.9925 | 1.0298 | 2.049 | 1.1954 | 0.9899 |
| 56 | 0.6297 | 1.6363 | 0.6303 | 1.0716 | 0.682 | 1.9891 | 1.0304 | 2.049 | 1.1994 | 0.9892 |
| 57 | 0.6296 | 1.6342 | 0.6298 | 1.0723 | 0.6815 | 1.9875 | 1.0307 | 2.0451 | 1.2009 | 0.9904 |
| 58 | 0.6283 | 1.6297 | 0.6292 | 1.072 | 0.6814 | 1.986 | 1.0308 | 2.0444 | 1.2021 | 0.9895 |
| 59 | 0.628 | 1.6284 | 0.6293 | 1.0737 | 0.681 | 1.9823 | 1.0313 | 2.0415 | 1.2046 | 0.99 |
| 60 | 0.6276 | 1.6253 | 0.6289 | 1.0732 | 0.6812 | 1.9797 | 1.0316 | 2.0402 | 1.2073 | 0.9886 |
| 61 | 0.6277 | 1.6238 | 0.6293 | 1.0744 | 0.6806 | 1.9759 | 1.0317 | 2.0373 | 1.2095 | 0.9902 |
| 62 | 0.6277 | 1.621 | 0.6292 | 1.0746 | 0.6802 | 1.9721 | 1.0321 | 2.034 | 1.2112 | 0.9902 |
| 63 | 0.6276 | 1.62 | 0.6291 | 1.0749 | 0.6801 | 1.9691 | 1.0324 | 2.0321 | 1.2148 | 0.9906 |
| 64 | 0.6274 | 1.6178 | 0.6291 | 1.0752 | 0.6798 | 1.9651 | 1.0328 | 2.0282 | 1.217 | 0.9902 |
| 65 | 0.627 | 1.6165 | 0.629 | 1.0758 | 0.6801 | 1.9623 | 1.0329 | 2.0269 | 1.2193 | 0.9902 |
| 66 | 0.6274 | 1.6142 | 0.6294 | 1.0758 | 0.6794 | 1.9583 | 1.0334 | 2.0218 | 1.221 | 0.9914 |
| 67 | 0.6271 | 1.6089 | 0.629 | 1.0758 | 0.68 | 1.9545 | 1.0344 | 2.0211 | 1.225 | 0.9909 |
| 68 | 0.6273 | 1.6082 | 0.6292 | 1.0762 | 0.6797 | 1.9506 | 1.0349 | 2.0188 | 1.2254 | 0.9915 |
| 69 | 0.6269 | 1.6032 | 0.6292 | 1.0759 | 0.6796 | 1.9485 | 1.035 | 2.0179 | 1.227 | 0.9907 |

A mathematical characteristic, a mean matrix μ for each column of $S_{ij}$ of the single gas sample was calculated according to the following equation;

$$\mu = \frac{1}{q} \Sigma S_{ij}, \mu \in R^{1 \times 10} \quad (1)$$

in this embodiment, q was the number of rows of $S_{ij}$ of the single gas sample, and q=15;

(2) Mean matrices μ of $S_{ij}$ of all gas samples were obtained according to step (1) to form a matrix P of all gas samples, wherein $P = \{X_1^N, X_2^N, \Lambda X_k^N\}$; $X_k^N \in R^{10 \times 10}$, and $X_k^N$ has 10 rows and 10 columns; $P \in R^{40 \times 10}$, and the matrix P has M·N rows (M·N=40) and 10 columns, as shown in Table. 3.

TABLE 3

Matrix P of trained gas samples (4 types of gas samples, 10 gas samples for each type, $p \in R^{40 \times 10}$)

| | No. | 1 | 2 | 3 | 4 | 5 | 6 | 7 | 8 | 9 | 10 |
|---|---|---|---|---|---|---|---|---|---|---|---|
| $X_1^{10}$ | 1 | 0.6452 | 1.6826 | 0.6446 | 1.0625 | 0.6959 | 2.0275 | 1.0211 | 2.0705 | 1.1421 | 0.9891 |
| ($CO_2$) | 2 | 0.6977 | 1.5034 | 0.7154 | 1.0612 | 0.7651 | 1.7297 | 1.0351 | 1.7297 | 1.1244 | 0.9869 |
| | 3 | 0.7266 | 1.3999 | 0.7507 | 1.0609 | 0.7977 | 1.5659 | 1.0459 | 1.5661 | 1.1308 | 0.9832 |
| | 4 | 0.7188 | 1.4277 | 0.7431 | 1.0794 | 0.7930 | 1.5857 | 1.0577 | 1.5869 | 1.1461 | 0.9920 |
| | 5 | 0.7294 | 1.4018 | 0.7568 | 1.0836 | 0.8046 | 1.5262 | 1.0591 | 1.5200 | 1.1466 | 0.9943 |
| | 6 | 0.7364 | 1.3816 | 0.7644 | 1.0887 | 0.8142 | 1.4755 | 1.0620 | 1.4698 | 1.1506 | 0.9989 |
| | 7 | 0.7470 | 1.3783 | 0.7739 | 1.0864 | 0.8214 | 1.4500 | 1.0590 | 1.4506 | 1.1413 | 0.9922 |
| | 8 | 0.7472 | 1.3714 | 0.7745 | 1.0908 | 0.8219 | 1.4237 | 1.0644 | 1.4340 | 1.1494 | 0.9914 |
| | 9 | 0.7461 | 1.3549 | 0.7719 | 1.0978 | 0.8214 | 1.4035 | 1.0730 | 1.4055 | 1.1655 | 0.9943 |
| | 10 | 0.7468 | 1.3587 | 0.7758 | 1.1037 | 0.8247 | 1.3987 | 1.0696 | 1.3937 | 1.1595 | 1.0056 |
| $X_2^{10}$ | 11 | 0.3924 | 2.5588 | 0.3480 | 1.6168 | 0.3612 | 2.4611 | 1.7678 | 2.6715 | 3.2760 | 0.9761 |
| ($CH_4$) | 12 | 0.4385 | 2.4131 | 0.3881 | 1.6144 | 0.3977 | 2.3901 | 1.5267 | 2.3956 | 2.2996 | 0.9738 |
| | 13 | 0.5688 | 1.5830 | 0.5321 | 1.4286 | 0.5605 | 1.6954 | 1.1031 | 1.6945 | 1.4743 | 0.9950 |
| | 14 | 0.5076 | 1.8246 | 0.4660 | 1.5436 | 0.4842 | 1.9230 | 1.2536 | 1.9618 | 1.8624 | 0.9900 |
| | 15 | 0.5034 | 1.8587 | 0.4593 | 1.5471 | 0.4754 | 1.9480 | 1.2792 | 1.9738 | 1.8807 | 0.9862 |
| | 16 | 0.5335 | 1.7179 | 0.4915 | 1.4997 | 0.5112 | 1.8023 | 1.2038 | 1.8239 | 1.7048 | 0.9888 |
| | 17 | 0.5157 | 1.7984 | 0.4704 | 1.5304 | 0.4864 | 1.8724 | 1.2619 | 1.9047 | 1.8408 | 0.9856 |
| | 18 | 0.5347 | 1.7054 | 0.4916 | 1.4977 | 0.5107 | 1.7715 | 1.2153 | 1.8029 | 1.7226 | 0.9885 |
| | 19 | 0.4431 | 2.3242 | 0.3924 | 1.6198 | 0.3947 | 2.2695 | 1.5508 | 2.3079 | 2.4276 | 0.9704 |
| | 20 | 0.4521 | 2.3053 | 0.3990 | 1.6160 | 0.4006 | 2.2407 | 1.4555 | 2.2435 | 2.2621 | 0.9700 |
| $X_3^{10}$ | 21 | 0.7334 | 4.4494 | 0.6842 | 1.3225 | 0.5755 | 2.1095 | 1.2121 | 1.8233 | 1.6389 | 0.9711 |
| ($NH_3$) | 22 | 0.7775 | 3.3309 | 0.7311 | 1.2630 | 0.6304 | 1.8399 | 1.0892 | 1.5862 | 1.2188 | 0.9746 |
| | 23 | 0.7929 | 2.9502 | 0.7507 | 1.2423 | 0.6491 | 1.7187 | 1.0614 | 1.4957 | 1.1969 | 0.9744 |
| | 24 | 0.8065 | 2.6620 | 0.7707 | 1.2310 | 0.6660 | 1.6161 | 1.0540 | 1.4192 | 1.1917 | 0.9749 |
| | 25 | 0.8079 | 2.5898 | 0.7734 | 1.2338 | 0.6685 | 1.5676 | 1.0585 | 1.3881 | 1.2081 | 0.9753 |
| | 26 | 0.8167 | 2.4470 | 0.7815 | 1.2246 | 0.6787 | 1.5063 | 1.0537 | 1.3430 | 1.1932 | 0.9774 |
| | 27 | 0.8119 | 2.5142 | 0.7756 | 1.2293 | 0.6738 | 1.4930 | 1.0621 | 1.3402 | 1.2154 | 0.9782 |
| | 28 | 0.8195 | 2.4827 | 0.7785 | 1.2116 | 0.6796 | 1.4694 | 1.0505 | 1.3144 | 1.1778 | 0.9781 |
| | 29 | 0.8234 | 2.4173 | 0.7826 | 1.2119 | 0.6854 | 1.4218 | 1.0523 | 1.2809 | 1.1827 | 0.9769 |
| | 30 | 0.8244 | 2.3943 | 0.7839 | 1.2125 | 0.6865 | 1.3963 | 1.0545 | 1.2600 | 1.1877 | 0.9762 |
| $X_4^{10}$ | 31 | 0.4764 | 2.3807 | 0.5024 | 1.0420 | 0.5607 | 2.1761 | 1.0587 | 2.1839 | 1.3539 | 1.0062 |
| (VOCs) | 32 | 0.5512 | 1.8220 | 0.5663 | 1.0523 | 0.6193 | 1.9041 | 1.0769 | 1.8710 | 1.3159 | 0.9976 |
| | 33 | 0.5818 | 1.5378 | 0.5941 | 1.0523 | 0.6488 | 1.7286 | 1.0883 | 1.7249 | 1.3466 | 0.9978 |
| | 34 | 0.5998 | 1.4691 | 0.6122 | 1.0571 | 0.6654 | 1.6609 | 1.0794 | 1.6712 | 1.3248 | 0.9974 |

TABLE 3-continued

| | Matrix P of trained gas samples (4 types of gas samples, 10 gas samples for each type, $p \in R^{40 \times 10}$) | | | | | | | | | |
|---|---|---|---|---|---|---|---|---|---|---|
| No. | 1 | 2 | 3 | 4 | 5 | 6 | 7 | 8 | 9 | 10 |
| 35 | 0.6058 | 1.4299 | 0.6181 | 1.0613 | 0.6713 | 1.6274 | 1.0858 | 1.6399 | 1.3314 | 0.9960 |
| 36 | 0.6032 | 1.4565 | 0.6153 | 1.0828 | 0.6691 | 1.6500 | 1.0883 | 1.6518 | 1.3403 | 1.0141 |
| 37 | 0.6039 | 1.4387 | 0.6147 | 1.0883 | 0.6698 | 1.5967 | 1.1082 | 1.6139 | 1.3695 | 1.0064 |
| 38 | 0.6110 | 1.4320 | 0.6187 | 1.0990 | 0.6700 | 1.5616 | 1.1191 | 1.5769 | 1.3767 | 1.0008 |
| 39 | 0.6135 | 1.4250 | 0.6217 | 1.1037 | 0.6721 | 1.5343 | 1.1213 | 1.5524 | 1.3799 | 0.9974 |
| 40 | 0.6155 | 1.4214 | 0.6204 | 1.1092 | 0.6725 | 1.5185 | 1.1195 | 1.5344 | 1.3744 | 0.9944 |

Secondly, a mathematical characteristic, a mean matrix $\mu_j$ for columns of $X_k^N$ of a single type of gas samples was calculated according to the following equation;

$$\mu_j = \frac{1}{N}\Sigma\mu, \; \mu_j \in R^{4 \times 10}, \; N \in [1, N] \quad (2)$$

the mean matrix $\mu_j$ was shown in Table 4.

TABLE 4

| | | Mean matrix $\mu_j$ of a single type of gas samples ($\mu_j \in R^{4 \times 10}$) | | | | | | | | | |
|---|---|---|---|---|---|---|---|---|---|---|---|
| No. | | 1 | 2 | 3 | 4 | 5 | 6 | 7 | 8 | 9 | 10 |
| 1 | $\mu_1$ ($CO_2$) | 0.7241 | 1.4260 | 0.7471 | 1.0815 | 0.7960 | 1.5586 | 1.0547 | 1.5627 | 1.1456 | 0.9928 |
| 2 | $\mu_2$ ($CH_4$) | 0.4890 | 2.0089 | 0.4438 | 1.5514 | 0.4583 | 2.0374 | 1.3618 | 2.0780 | 2.0751 | 0.9824 |
| 3 | $\mu_3$ ($CH_4$) | 0.8014 | 2.8238 | 0.7612 | 1.2383 | 0.6594 | 1.6139 | 1.0748 | 1.4251 | 1.2411 | 0.9757 |
| 4 | $\mu_4$ ($CH_4$) | 0.5862 | 1.5813 | 0.5984 | 1.0748 | 0.6519 | 1.6958 | 1.0946 | 1.7020 | 1.3513 | 1.0008 |

A mean matrix $\mu_k$ of the matrix P of all gas samples was calculated according to the following equation;

$$\mu_k = \frac{1}{K}\Sigma\mu_j, \; \mu_k \in R^{1 \times 10}, \; K \in [1, K] \quad (3)$$

the mean matrix $\mu_k$ was shown in Table 5.

TABLE 5

| | | Mean matrix $\mu_k$ of the matrix P of all gas samples ($\mu_k \in R^{1 \times 10}$) | | | | | | | | | |
|---|---|---|---|---|---|---|---|---|---|---|---|
| No. | | 1 | 2 | 3 | 4 | 5 | 6 | 7 | 8 | 9 | 10 |
| 1 | $\mu_k$ | 0.6502 | 1.9600 | 0.6376 | 1.2365 | 0.6414 | 1.7264 | 1.1465 | 1.6920 | 1.4533 | 0.9879 |

A within-class scatter matrix $J_W$ and a between-class scatter matrix $J_B$ of the matrix P of all gas samples were respectively calculated according to the following equations:

$$J_W = \sum_{N=1}^{N}\sum_{K=1}^{K}(\mu_j - X_K^N)^T(\mu_j - X_K^N), \; J_W \in R^{10 \times 10} \quad (4)$$

$$J_B = \sum_{K=1}^{K}(\mu_K - \mu_j)^T(\mu_K - \mu_j), \; J_B \in R^{10 \times 10} \quad (5)$$

the matrix $J_W$ was shown in Table 6 and the matrix $J_B$ was shown in Table 7.

TABLE 6

Within-class scatter matrix $J_W$ of matrix P ($J_W \in R^{10 \times 10}$)

| No. | 1 | 2 | 3 | 4 | 5 | 6 | 7 | 8 | 9 | 10 |
|---|---|---|---|---|---|---|---|---|---|---|
| 1 | 0.0600 | −0.4773 | 0.0630 | −0.0287 | 0.0658 | −0.3226 | −0.1008 | −0.3296 | −0.2712 | 0.0046 |
| 2 | −0.4773 | 5.7451 | −0.5051 | 0.3304 | −0.5340 | 2.8284 | 0.8493 | 2.6514 | 2.2276 | −0.0355 |
| 3 | 0.0630 | −0.5051 | 0.0675 | −0.0324 | 0.0707 | −0.3437 | −0.1081 | −0.3503 | −0.2869 | 0.0054 |
| 4 | −0.0287 | 0.3304 | −0.0324 | 0.0559 | −0.0380 | 0.1607 | 0.1278 | 0.1607 | 0.2923 | −0.0048 |
| 5 | 0.0658 | −0.5340 | 0.0707 | −0.0380 | 0.0746 | −0.3600 | −0.1201 | −0.3657 | −0.3129 | 0.0061 |
| 6 | −0.3226 | 2.8284 | −0.3437 | 0.1607 | −0.3600 | 1.8375 | 0.5207 | 1.8191 | 1.3750 | −0.0266 |
| 7 | −0.1008 | 0.8493 | −0.1081 | 0.1278 | −0.1201 | 0.5207 | 0.4069 | 0.5795 | 1.0032 | −0.0145 |
| 8 | −0.3296 | 2.6514 | −0.3503 | 0.1607 | −0.3657 | 1.8191 | 0.5795 | 1.8620 | 1.5601 | −0.0271 |
| 9 | −0.2712 | 2.2276 | −0.2869 | 0.2923 | −0.3129 | 1.3750 | 1.0032 | 1.5601 | 2.5957 | −0.0328 |
| 10 | 0.0046 | −0.0355 | 0.0054 | −0.0048 | 0.0061 | −0.0266 | −0.0145 | −0.0271 | −0.0328 | 0.0015 |

TABLE 7

Between-class scatter matrix $J_B$ of matrix P ($J_B \in R^{10 \times 10}$)

| No. | 1 | 2 | 3 | 4 | 5 | 6 | 7 | 8 | 9 | 10 |
|---|---|---|---|---|---|---|---|---|---|---|
| 1 | 0.0447 | −0.0481 | 0.0476 | −0.0356 | 0.0344 | −0.0739 | −0.0276 | −0.0893 | −0.0920 | −0.0015 |
| 2 | −0.0481 | 2.8878 | −0.1012 | 0.0525 | −0.0803 | 0.1393 | −0.0809 | −0.0932 | −0.1674 | 0.0091 |
| 3 | 0.0476 | −0.1012 | 0.0531 | −0.0482 | 0.0426 | −0.0868 | −0.0329 | −0.0986 | −0.1089 | −0.0010 |
| 4 | −0.0356 | 0.0525 | −0.0482 | 0.1030 | −0.0620 | 0.1122 | 0.0612 | 0.1235 | 0.1833 | −0.0039 |
| 5 | 0.0344 | −0.0803 | 0.0426 | −0.0620 | 0.0480 | −0.0910 | −0.0372 | −0.0973 | −0.1208 | 0.0015 |
| 6 | −0.0739 | 0.1393 | −0.0868 | 0.1122 | −0.0910 | 0.2035 | 0.0655 | 0.2220 | 0.2226 | −0.0020 |
| 7 | −0.0276 | −0.0809 | −0.0329 | 0.0612 | −0.0372 | 0.0655 | 0.0435 | 0.0849 | 0.1276 | −0.0020 |
| 8 | −0.0893 | −0.0932 | −0.0986 | 0.1235 | −0.0973 | 0.2220 | 0.0849 | 0.2686 | 0.2768 | −0.0021 |
| 9 | −0.0920 | −0.1674 | −0.1089 | 0.1833 | −0.1208 | 0.2226 | 0.1276 | 0.2768 | 0.3845 | −0.0054 |
| 10 | −0.0015 | 0.0091 | −0.0010 | −0.0039 | 0.0015 | −0.0020 | −0.0020 | −0.0021 | −0.0054 | 0.0005 |

Finally, an objective optimization function $\phi(\omega)$ of the matrix P was calculated, wherein $\phi(\omega)$ was expressed as $$\phi(\omega) = \frac{\omega J_B \omega^T}{\omega J_W \omega^T} \quad (6)$$

When $\phi(\omega)$ took the maximum value, the eigenvalue $\omega$ satisfied a maximum $J_B$ value and a minimum $J_W$ value, so that conditions for the optimization of the matrix P were satisfied.

The eigenvalue was set as $\lambda$, and $\omega J_W \omega^T = 1$ was plugged into the equation (6), as shown in formula (7), $$\begin{cases} \phi(\omega) = \frac{\omega J_B \omega^T}{\omega J_W \omega^T} \\ \omega J_W \omega^T = 1 \end{cases} \quad (7)$$

Thus, the equation (6) was converted by Lagrange multiplier method to obtain the following equation:

$$\phi(\omega)' = \omega J_B \omega^T - \lambda(\omega J_W \omega^T - 1) \quad (8)$$

The derivation was performed on $\omega$ on both sides of the equal sign of the equation (8) to solve the eigenvalue of the matrix formed from $J_B$ and $J_W$, as shown in the following equation:

$$\frac{d\phi(\omega)'}{d\omega} = 2J_B\omega - 2\lambda J_W \omega = 0 \quad (9)$$

to obtain $\lambda = J_B J_W^{-1}$, $\lambda \in R^{10 \times 10}$; $\quad (10)$ The eigenvalue $\lambda$ of the optimization function was shown in Table 8.

TABLE 8

Eigenvalue $\lambda$ of optimization function ($\lambda \in R^{10 \times 10}$)

| No. | 1 | 2 | 3 | 4 | 5 | 6 | 7 | 8 | 9 | 10 |
|---|---|---|---|---|---|---|---|---|---|---|
| 1 | −0.1195 | −0.1542 | 0.3811 | −0.4359 | 0.6008 | −0.1975 | −0.1975 | 0.0631 | 0.0125 | −0.0004 |
| 2 | −0.0083 | −0.0388 | 0.0078 | −0.0392 | −0.0191 | 0.0013 | 0.0013 | 0.0127 | 0.0241 | −0.0051 |
| 3 | −0.6898 | 0.1441 | −0.3584 | 0.4345 | −0.7467 | 0.1270 | 0.1270 | 0.1043 | 0.0216 | 0.0995 |
| 4 | 0.0564 | 0.2378 | −0.3123 | −0.2586 | −0.0708 | −0.0921 | −0.0921 | −0.1140 | −0.1233 | 0.0835 |
| 5 | 0.6801 | −0.7214 | −0.5732 | −0.4477 | 0.1518 | 0.1607 | 0.1607 | −0.2709 | −0.0010 | −0.0680 |
| 6 | 0.0654 | 0.1836 | 0.0681 | 0.2879 | 0.1120 | 0.1705 | 0.1705 | −0.0922 | −0.1942 | 0.0002 |
| 7 | −0.0323 | −0.4124 | 0.0890 | −0.0028 | 0.1353 | 0.0322 | 0.0322 | 0.8005 | 0.0107 | −0.0970 |

TABLE 8-continued

Eigenvalue $\lambda$ of optimization function ($\lambda \in R^{10 \times 10}$)

| No. | 1 | 2 | 3 | 4 | 5 | 6 | 7 | 8 | 9 | 10 |
|---|---|---|---|---|---|---|---|---|---|---|
| 8 | −0.0833 | −0.2845 | −0.1938 | −0.3344 | −0.1448 | −0.1490 | −0.1490 | 0.1447 | 0.1851 | −0.0052 |
| 9 | 0.0197 | 0.1586 | 0.0115 | 0.0658 | 0.0020 | 0.0729 | 0.0729 | −0.2918 | 0.0403 | 0.0144 |
| 10 | −0.1776 | 0.2593 | 0.4999 | 0.3915 | −0.0345 | −0.6134 | −0.6134 | 0.3784 | −0.9539 | 0.9843 |

(3) A recognition feature matrix $M_{train}$ was calculated according to the following equation:

$$M_{train} = P \times \lambda M_{train} \in R^{M \cdot N \times 10} \quad (11).$$

Figure 4:
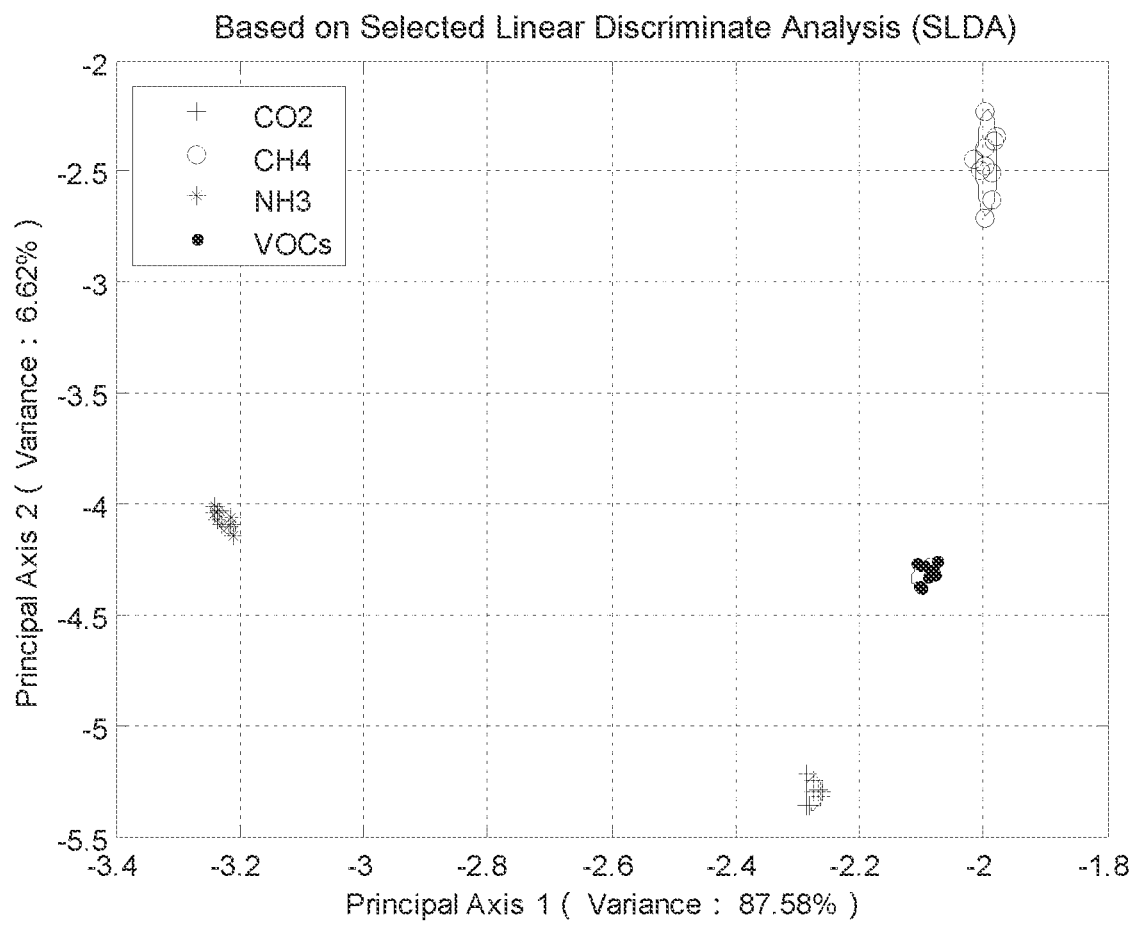
FIG. 4 shows the results of classifying various gases according to an embodiment of the present invention.

The first two columns of the recognition feature matrix $M_{train}$ were selected for two-dimensional classification purpose, as shown in Table 9. As shown in FIG. 4, Principal Axis 1 was the first column of $M_{train}$ and Principal Axis 2 was the second column of $M_{train}$.

TABLE 9

Recognition feature matrix $M_{train}$
(4 types of gas samples, 10 gas samples for each type, $M_{train} \in R^{40 \times 10}$)

| No. | | 1 Principal Axis 1 | 2 Principal Axis 2 | 3 | 4 | 5 | 6 | 7 | 8 | 9 | 10 |
|---|---|---|---|---|---|---|---|---|---|---|---|
| 1 | $X_1^{10}$ | −2.2838 | −5.2148 | −3.6742 | −3.0252 | −0.6182 | −4.8262 | −4.8262 | 7.9090 | −9.6611 | 9.7734 |
| 2 | ($CO_2$) | −2.2652 | −5.2954 | −3.6774 | −2.9211 | −0.5119 | −4.7247 | −4.7247 | 7.7438 | −9.7188 | 9.7840 |
| 3 | | −2.2797 | −5.3643 | −3.6905 | −2.9334 | −0.4630 | −4.6904 | −4.6904 | 7.6658 | −9.6783 | 9.7641 |
| 4 | | −2.2626 | −5.3205 | −3.6922 | −2.9385 | −0.4733 | −4.7451 | −4.7451 | 7.7431 | −9.7734 | 9.8502 |
| 5 | | −2.2740 | −5.2987 | −3.6807 | −2.9161 | −0.4610 | −4.7492 | −4.7492 | 7.7010 | −9.8106 | 9.8854 |
| 6 | | −2.2646 | −5.2918 | −3.6650 | −2.9194 | −0.4426 | −4.7790 | −4.7790 | 7.6820 | −9.8558 | 9.9373 |
| 7 | | −2.2845 | −5.3626 | −3.7104 | −2.9908 | −0.4393 | −4.7557 | −4.7557 | 7.6548 | −9.7766 | 9.8766 |
| 8 | | −2.2845 | −5.3651 | −3.7129 | −3.0181 | −0.4413 | −4.7662 | −4.7662 | 7.6650 | −9.7517 | 9.8697 |
| 9 | | −2.2576 | −5.2989 | −3.6626 | −2.9751 | −0.4015 | −4.7701 | −4.7701 | 7.6631 | −9.7988 | 9.8982 |
| 10 | | −2.2734 | −5.2471 | −3.6386 | −2.9267 | −0.4232 | −4.8320 | −4.8320 | 7.6728 | −9.9274 | 10.0188 |
| 11 | $X_2^{10}$ | −1.9870 | −2.5021 | −3.3437 | −2.9186 | −0.3170 | −4.0205 | −4.0205 | 7.9982 | −8.8918 | 9.5503 |
| 12 | ($CH_4$) | −1.9869 | −2.6335 | −3.3765 | −2.9723 | −0.2798 | −4.4869 | −4.4869 | 8.5306 | −9.6796 | 9.6552 |
| 13 | | −1.9984 | −2.7095 | −3.2939 | −2.9418 | −0.3947 | −5.1477 | −5.1477 | 7.1514 | −10.1338 | 10.1101 |
| 14 | | −1.9805 | −2.3408 | −3.4027 | −3.0195 | −0.4312 | −4.9842 | −4.9842 | 7.3807 | −9.9655 | 10.0274 |
| 15 | | −1.9815 | −2.3600 | −3.3528 | −2.9851 | −0.3819 | −4.9317 | −4.9317 | 7.5267 | −9.9435 | 9.9678 |
| 16 | | −1.9965 | −2.4788 | −3.3047 | −2.9806 | −0.3792 | −5.0445 | −5.0445 | 7.3553 | −10.0069 | 10.0238 |
| 17 | | −1.9955 | −2.3944 | −3.3019 | −2.9876 | −0.3594 | −4.9666 | −4.9666 | 7.4729 | −9.9269 | 9.9690 |
| 18 | | −2.0045 | −2.4936 | −3.2619 | −2.9813 | −0.3578 | −5.0486 | −5.0486 | 7.3952 | −9.9751 | 10.0127 |
| 19 | | −2.0144 | −2.4427 | −3.2741 | −2.9230 | −0.2473 | −4.4546 | −4.4546 | 8.3195 | −9.5478 | 9.6365 |
| 20 | | −1.9974 | −2.2315 | −3.2874 | −2.9182 | −0.2984 | −4.5533 | −4.5533 | 7.9699 | −9.6815 | 9.7048 |
| 21 | $X_3^{10}$ | −3.2374 | −4.0720 | −2.7133 | −3.1410 | −0.5558 | −4.3038 | −4.3038 | 7.9642 | −9.5175 | 9.6933 |
| 22 | ($NH_3$) | −3.2088 | −4.1474 | −2.7940 | −3.0259 | −0.4362 | −4.6769 | −4.6769 | 7.9788 | −9.8301 | 9.8145 |
| 23 | | −3.2141 | −4.0652 | −2.8133 | −2.9497 | −0.4169 | −4.7339 | −4.7339 | 7.7550 | −9.8326 | 9.8495 |
| 24 | | −3.2387 | −4.0416 | −2.8436 | −2.8964 | −0.4101 | −4.7718 | −4.7718 | 7.6567 | −9.8324 | 9.8782 |
| 25 | | −3.2392 | −4.0154 | −2.8415 | −2.9043 | −0.4092 | −4.7961 | −4.7961 | 7.6306 | −9.8127 | 9.8887 |
| 26 | | −3.2371 | −4.0401 | −2.8278 | −2.9005 | −0.3784 | −4.8428 | −4.8428 | 7.6136 | −9.8241 | 9.9148 |
| 27 | | −3.2331 | −4.0345 | −2.7959 | −2.9332 | −0.3861 | −4.8567 | −4.8567 | 7.6346 | −9.7926 | 9.9158 |
| 28 | | −3.2276 | −4.0957 | −2.7389 | −2.9281 | −0.3402 | −4.8751 | −4.8751 | 7.6437 | −9.7943 | 9.9077 |
| 29 | | −3.2162 | −4.1065 | −2.7494 | −2.9549 | −0.3282 | −4.8892 | −4.8892 | 7.6171 | −9.7651 | 9.9002 |
| 30 | | −3.2143 | −4.0941 | −2.7381 | −2.9541 | −0.3212 | −4.8923 | −4.8923 | 7.6061 | −9.7512 | 9.8951 |
| 31 | $X_4^{10}$ | −2.0885 | −4.3279 | −2.8894 | −2.2685 | −0.8433 | −4.7165 | −4.7165 | 7.9071 | −9.6702 | 9.8287 |
| 32 | (VOCs) | −2.0832 | −4.2999 | −2.8553 | −2.1830 | −0.5073 | −4.6724 | −4.6724 | 7.8015 | −9.7776 | 9.7971 |
| 33 | | −2.0784 | −4.3141 | −2.8514 | −2.2123 | −0.4009 | −4.7106 | −4.7106 | 7.6866 | −9.7547 | 9.8217 |
| 34 | | −2.1037 | −4.3680 | −2.9176 | −2.3030 | −0.4034 | −4.7536 | −4.7536 | 7.6332 | −9.7450 | 9.8400 |
| 35 | | −2.1000 | −4.3781 | −2.9286 | −2.3185 | −0.3808 | −4.7479 | −4.7479 | 7.6297 | −9.7339 | 9.8299 |
| 36 | | −2.1089 | −4.2631 | −2.8949 | −2.2736 | −0.3938 | −4.8522 | −4.8522 | 7.6689 | −9.9455 | 10.0217 |
| 37 | | −2.0866 | −4.2959 | −2.8929 | −2.3278 | −0.3592 | −4.8180 | −4.8180 | 7.6975 | −9.8360 | 9.9371 |
| 38 | | −2.0990 | −4.2817 | −2.8850 | −2.3621 | −0.3213 | −4.7981 | −4.7981 | 7.7164 | −9.7919 | 9.8874 |
| 39 | | −2.0967 | −4.2758 | −2.8992 | −2.3867 | −0.3184 | −4.7865 | −4.7865 | 7.6943 | −9.7568 | 9.8593 |
| 40 | | −2.0745 | −4.2560 | −2.8998 | −2.4163 | −0.2924 | −4.7828 | −4.7828 | 7.6652 | −9.7410 | 9.8348 |

(4) Each type of gas samples remained 10 gas samples. Among these 10 gas samples, 2 gas samples were randomly selected for test purpose, thus there were 4 types of gas samples to be tested, and each type had 2 samples. A recognition feature matrix $M_{test}$ of the gas samples to be tested was obtained by repeating steps (1)-(3) of the selected linear discriminate analysis. By using a two-dimensional distance discriminant method and comparing $M_{test}$ and $M_{train}$, the type of the gas samples to be tested was identified.

In this embodiment, the two-dimensional distance discriminant method in step (4) further included the following steps.

(1) A recognition feature matrix of trained gas samples was set as $M_{train}$, and a recognition feature matrix of each type of trained gas samples was set as $M_{traink}$, and then a mean matrix $A_{traink}$ for all columns of $M_{traink}$ were calculated according to the following equation:

$$A_{traink} = \sum_{i=1}^{N} M_{traink}, A_{traink} \in R^{1\times 10} \quad (12)$$

the first two columns of $A_{traink}$ were extracted and saved as $A_{traink12}$ which was expressed as $$A_{traink12}=(x_{i1},x_{i2}) \quad (13);$$

The matrix $A_{train12}$ was shown in Table 10.

TABLE 10

Recognition matrix $A_{train12}$ of trained gas samples (extracted from the first two columns of $A_{traink}$)

| No. | | 1 $X_{i1}$ | 2 $X_{i2}$ | 3 | 4 | 5 | 6 | 7 | 8 | 9 | 10 |
|---|---|---|---|---|---|---|---|---|---|---|---|
| 1 | $A_{train1}$ ($CO_2$) | −2.2729 | −5.3059 | −3.6804 | −2.9564 | −0.4675 | −4.7638 | −4.7638 | −7.7100 | −9.7753 | 9.8657 |
| 2 | $A_{train2}$ ($CH_4$) | −1.9942 | −2.4587 | −3.3199 | −2.9627 | −0.3446 | −4.7638 | −4.7638 | −7.7100 | −9.7753 | 9.8657 |
| 3 | $A_{train3}$ ($NH_3$) | −3.2266 | −4.0712 | −2.7855 | −2.9558 | −0.3983 | −4.7638 | −4.7638 | −7.7100 | −9.7753 | 9.8657 |
| 4 | $A_{train4}$ (VOCs) | −2.0919 | −4.3060 | −2.8914 | −2.3052 | −0.4201 | −4.7638 | −4.7638 | −7.7100 | −9.7753 | 9.8657 |

(2) A recognition feature matrix of gas samples to be tested was set as $M_{test}$, and the first two columns of $M_{test}$ were saved as $A_{testk12}$ which was expressed as the following equation:

$$A_{testk12}=(x_{j1},x_{j2}) \quad (14);$$

The matrix $M_{testk}$ was shown in Table 11.

TABLE 11

Recognition feature matrix $M_{testk}$ (4 types of gas samples, 2 samples for each type, $M_{test} \in R^{8\times 10}$)

| No. | | 1 $X_{j1}$ | 2 $X_{j2}$ | 3 | 4 | 5 | 6 | 7 | 8 | 9 | 10 |
|---|---|---|---|---|---|---|---|---|---|---|---|
| 1 | $A_{test1}$ | −2.0827 | −4.2206 | −2.8834 | −2.4072 | −0.2898 | −4.7768 | −4.7768 | 7.6581 | −9.7348 | 9.8294 |
| 2 | | −2.0803 | −4.2121 | −2.8953 | −2.4236 | −0.2877 | −4.7769 | −4.7769 | 7.6095 | −9.7308 | 9.8258 |
| 3 | $A_{test2}$ | −1.9973 | −2.1485 | −3.2804 | −2.9078 | −0.3129 | −4.5743 | −4.5743 | 7.8599 | −9.6980 | 9.7244 |
| 4 | | −1.9974 | −2.1078 | −3.2656 | −2.9107 | −0.3130 | −4.6006 | −4.6006 | 7.7979 | −9.7074 | 9.7415 |
| 5 | $A_{test3}$ | −3.2170 | −4.1286 | −2.7121 | −2.9509 | −0.3017 | −4.9078 | −4.9078 | 7.5987 | −9.7413 | 9.8926 |
| 6 | | −3.2355 | −4.0775 | −2.7273 | −2.9425 | −0.3138 | −4.9163 | −4.9163 | 7.5828 | −9.7246 | 9.9027 |
| 7 | $A_{test4}$ | −2.2714 | −5.3311 | −3.6646 | −3.0084 | −0.4102 | −4.7877 | −4.7877 | 7.6737 | −9.7731 | 9.9010 |
| 8 | | −2.2804 | −5.3646 | −3.6856 | −3.0382 | −0.4024 | −4.7800 | −4.7800 | 7.6316 | −9.7455 | 9.8844 |

(3) A two-dimensional spatial distance d of $A_{traink12}$ and $A_{testk12}$ was calculated according to the following equation:

$$d=\sqrt{(x_{j1}-x_{i1})^2+(x_{j2}-x_{i2})^2} \quad (15);$$

and d values and identification results were shown in table 12.

TABLE 12

Two-dimensional spatial distance d values and identification results

| No. | | 1 $X_{j1}$ | 2 $X_{j2}$ | No. | 1 $X_{i1}$ | 2 $X_{i2}$ | $d_{test1}$ | $d_{test2}$ | $d_{test3}$ | $d_{test4}$ | Identification results |
|---|---|---|---|---|---|---|---|---|---|---|---|
| 1 | $A_{test1}$ | −2.0827 | −4.2206 | $A_{train4}$ (VOCs) | −2.0919 | −4.3060 | 0.0859 | 1.7641 | 1.1536 | 1.1102 | VOCs |
| 2 | | −2.0803 | −4.2121 | | | | 0.0946 | 1.7555 | 1.1549 | 1.1106 | VOCs |
| 3 | $A_{test2}$ | −1.9973 | −2.1485 | $A_{train2}$ ($CH_4$) | −1.9942 | −2.4587 | 2.1596 | 0.3102 | 2.3164 | 3.1694 | $CH_4$ |
| 4 | | −1.9974 | −2.1078 | | | | 2.2002 | 0.3509 | 0.0582 | 3.2099 | $CH_4$ |

TABLE 12-continued

Two-dimensional spatial distance d values and identification results

| No. | | 1<br>$X_{j1}$ | 2<br>$X_{j2}$ | No. | 1<br>$X_{i1}$ | 2<br>$X_{i2}$ | $d_{test1}$ | $d_{test2}$ | $d_{test3}$ | $d_{test4}$ | Identification results |
|---|---|---|---|---|---|---|---|---|---|---|---|
| 5 | $A_{test3}$ | −3.2170 | −4.1286 | $A_{train3}$ | −3.2266 | −4.0712 | 1.1390 | 2.0697 | 0.0109 | 1.5091 | $NH_3$ |
| 6 | | −3.2355 | −4.0775 | ($NH_3$) | | | 1.1662 | 2.0399 | 0.0109 | 1.5606 | $NH_3$ |
| 7 | $A_{test4}$ | −2.2714 | −5.3311 | $A_{train1}$ | −2.2729 | −5.3059 | 1.0407 | 2.8857 | 1.5811 | 0.0252 | $CO_2$ |
| 8 | | −2.2804 | −5.3646 | ($CO_2$) | | | 1.0753 | 2.9200 | 1.6026 | 0.0592 | $CO_2$ |

Figure 5:
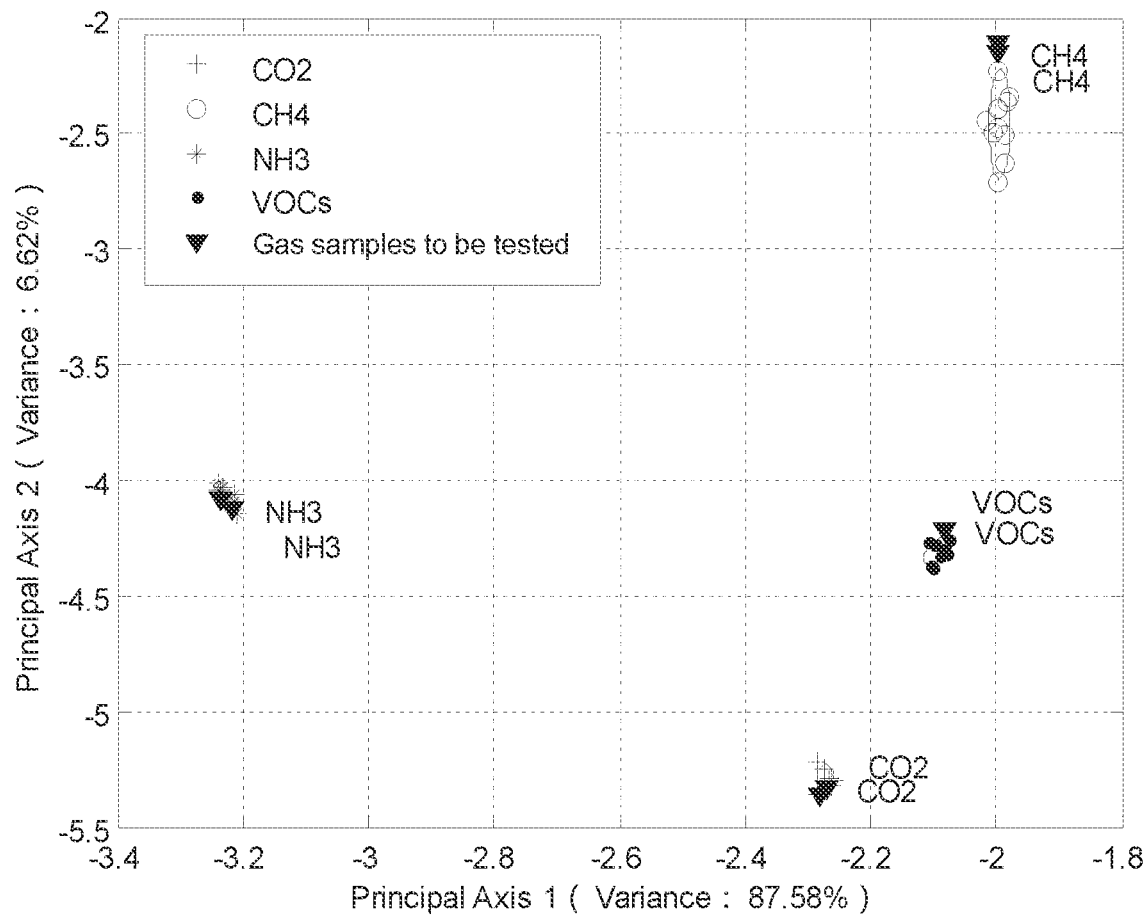
FIG. 5 shows the results of identifying various gases according to an embodiment of the present invention.

In this embodiment, two-dimensional spatial distances d of the matrix $A_{testk}$ of the gas samples to be test and the matrix $A_{traink}$ of the trained gas samples were respectively calculated, where d being close to 0 indicated that the gas sample to be tested and the trained gas sample are identified as the same type of gas. It can be seen from Table 12, the first type of the gas samples to be tested was VOCs, and the second type of the gas samples to be tested was $CH_4$, the third type of the gas samples to be tested was $NH_3$, and the fourth type of the gas samples to be tested was $CO_2$. In FIG. 5, $(X_{j1}, X_{j2})$ was a center point of each type of the trained gas samples, and $X_{j1}$ was the abscissa data, $X_{j2}$ was the ordinate data; and $(X_{i1}, X_{i2})$ was the classification point of respective gas samples to be tested, and $X_{i1}$ was the abscissa data, and $X_{i2}$ was the ordinate data.

The same or similar reference numerals correspond to the same or similar parts.

The terms for describing the positional relationship in the drawings are illustrative only, and are not intended to limit the present invention;

Obviously, the above are some exemplary embodiments of the invention, which are merely for the purpose of illustration, and are not intended to limit the present invention. Other modifications or variations can be made by those skilled in the art based on the above descriptions. All these modifications, equivalent replacements and improvements made within the spirit and principle of the present invention shall fall within the scope of the appended claims of the present invention.

What is claimed is:

1. A method for detecting and identifying toxic and harmful gases based on machine olfaction, comprising:
   (1) collecting and placing a gas sample in a constant temperature and humidity device;
   (2) delivering the gas sample to a sensor chamber to contact a sensor array to obtain measurement data, wherein the sensor array integrates multiple types of gas sensors; performing A/D conversion on the measurement data through an A/D acquisition card; and transferring the converted data to a computer and saving the data as $S_{data}$;
   (3) performing data feature extraction on the collected data $S_{data}$, and obtaining a recognition feature matrix $M_{train}$ through a selected linear discriminate analysis; and
   (4) repeating steps (1)-(3) to obtain a recognition feature matrix $M_{test}$ of a gas sample; and comparing $M_{test}$ and $M_{train}$ by using a two-dimensional distance discriminant method to identify the type of the gas sample;
   wherein the selected linear discriminate analysis in step (3) comprises the following steps:
   (a) classifying gas samples into K types each having N gas samples; setting the collected and measured data of single gas sample as $S_{data1}$, wherein $S_{data1} \in R^{120 \times 10}$, and $S_{data1}$ has 120 rows and 10 columns; selecting and saving data from rows 55-69 of $S_{data1}$ as $S_{ij}$, wherein $S_{ij} \in R^{15 \times 10}$, and $S_{ij}$ has 15 rows and 10 columns; calculating a mathematical characteristic, a mean matrix μ for each column of $S_{ij}$ of the single gas sample according to the following equation;

$$\mu = \frac{1}{q} \Sigma S_{ij}, \mu \in R^{1 \times 10} \quad (1)$$

wherein q is the number of rows of $S_{ij}$ of the single gas sample, and q=15;
   (b) obtaining mean matrices μ of $S_{ij}$ of all gas samples according to step (1) to form a matrix P of all gas samples, wherein $P = \{X_1^N, X_2^N, \ldots X_k^N\}$; $X_k^N \in R^{N \times 10}$, and $X_k^N$ has N rows and 10 columns; $P \in R^{M \cdot N \times 10}$, and the matrix P has M·N rows and 10 columns, calculating a mathematical characteristic, a mean matrix $\mu_j$ for columns of $X_k^N$ of a single type of gas samples according to the following equation;

$$\mu_j = \frac{1}{N} \Sigma \mu, \mu_j \in R^{K \times 10}, N \in [1, N] \quad (2)$$

then calculating a mean matrix $\mu_k$ of the matrix P of all gas samples according to the following equation;

$$\mu_k = \frac{1}{K} \Sigma \mu_j, \mu_k \in R^{1 \times 10}, K \in [1, K] \quad (3)$$

then calculating a within-class scatter matrix $J_W$ and a between-class scatter matrix $J_B$ of the matrix P of all gas samples according to the following equations;

$$J_W = \sum_{N=1}^{N} \sum_{K=1}^{K} (\mu_j - X_K^N)^T (\mu_j - X_K^N), J_W \in R^{10 \times 10} \quad (4)$$

$$J_B = \sum_{K=1}^{K} (\mu_K - \mu_j)^T (\mu_K - \mu_j), J_B \in R^{10 \times 10} \quad (5)$$

and calculating an objective optimization function φ(ω) of the matrix P,
wherein φ(ω) is expressed as $$\phi(\omega) = \frac{\omega J_B \omega^T}{\omega J_W \omega^T} \quad (6)$$

when $\phi(\omega)$ takes the maximum value, the eigenvalue $\omega$ satisfies a maximum $J_B$ value and a minimum $J_W$ value, so that conditions for the optimization of the matrix P are satisfied;

setting the eigenvalue as $\lambda$, plugging $\omega J_W \omega^T = 1$ into the equation (6), as shown in formula (7), $$\begin{cases} \phi(\omega) = \dfrac{\omega J_B \omega^T}{\omega J_W \omega^T} \\ \omega J_W \omega^T = 1 \end{cases} \quad (7)$$

thus converting the equation (6) by Lagrange multiplier method to obtain the following equation;

$$\phi(\omega)' = \omega J_B \omega^T - \lambda(\omega J_W \omega^T - 1) \quad (8)$$

performing derivation on $\omega$ on both sides of the equation (8) to solve the eigenvalue of the matrix formed from $J_B$ and $J_W$, as shown in the following equation;

$$\frac{d\phi(\omega)'}{d\omega} = 2J_B \omega - 2\lambda J_W \omega = 0 \quad (9)$$

to obtain $\lambda = J_B J_W^{-1}, \lambda \in R^{10 \times 10}$; (10)

and (c) calculating a recognition feature matrix $M_{train}$ according to the following equation;

$$M_{train} = P \times \lambda, M_{train} \in R^{M \cdot N \times 10} \quad (11).$$

2. The method of claim 1, wherein step (1) comprises the following steps:

collecting and storing the gas sample in a sampling bag through an electric air pump; and then delivering the gas sample in the sampling bag via a gas valve to a gas chamber provided in the constant temperature and humidity device.

3. The method of claim 2, wherein in step (1), a hole diameter of the gas valve is 5 mm; a volume of the sampling bag is 600 ml; a volume of the gas chamber is 600 ml; the gas is delivered to the gas chamber at a flow rate of 5 ml/s; the constant temperature and humidity device is Type ZH-TH-80 with an internal dimension of 400×500×400 mm and an external dimension of 1050×1650×980 mm, and is set with a temperature of 30° C., and a relative humidity of 50-60%.

4. The method of claim 1, wherein in step (2), the sensor array consists of 10 metal oxide gas sensors which are uniformly arranged in a circle with a diameter of 10.2 cm; a gas sampling time is 120 s; and the A/D acquisition card is Type AD7705.

5. A method for detecting and identifying toxic and harmful gases based on machine olfaction, comprising:

(1) collecting and placing a gas sample in a constant temperature and humidity device;

(2) delivering the gas sample to a sensor chamber to contact a sensor array to obtain measurement data, wherein the sensor array integrates multiple types of gas sensors; performing A/D conversion on the measurement data through an A/D acquisition card; and transferring the converted data to a computer and saving the data as $S_{data}$;

(3) performing data feature extraction on the collected data $S_{data}$, and obtaining a recognition feature matrix $M_{train}$ through a selected linear discriminate analysis; and (4) repeating steps (1)-(3) to obtain a recognition feature matrix $M_{test}$ of a gas sample; and comparing $M_{test}$ and $M_{train}$ by using a two-dimensional distance discriminant method to identify the type of the gas sample;

wherein the two-dimensional distance discriminant method in step (4) comprises the following steps:

(a) setting a recognition feature matrix of trained gas samples as $M_{train}$, and setting a recognition feature matrix of each type of trained gas samples as $M_{traink}$, and calculating a mean matrix $A_{traink}$, for all columns of $M_{traink}$, according to the following equation:

$$A_{traink} = \sum_{i=1}^{N} M_{traink}, A_{traink} \in R^{1 \times 10} \quad (12)$$

extracting the first two columns of $A_{traink}$, to obtain $A_{traink12}$ which is expressed as $$A_{traink12} = (x_{i1}, x_{i2}) \quad (13);$$

(b) setting a recognition feature matrix of gas samples to be tested as $M_{test}$, and extracting the first two columns of $M_{test}$ as $A_{testkl2}$, which is expressed as:

$$A_{traink12} = (x_{j1}, x_{j2}) \quad (14);$$

and (c) calculating a two-dimensional spatial distance d of $A_{train12}$ and $A_{testkl2}$ according to the following equation:

$$d = \sqrt{(x_{j1} - x_{i1})^2 + (x_{j2} - x_{i2})^2} \quad (15);$$

wherein d being close to 0 indicates a close spatial distance, indicating that the gas sample to be tested and the trained gas sample are identified as the same type of gas.

* * * * *